(12) United States Patent
Soper et al.

(10) Patent No.: US 12,564,449 B2
(45) Date of Patent: Mar. 3, 2026

(54) SYSTEMS AND METHODS FOR REGISTRATION OF PATIENT ANATOMY

(71) Applicant: Intuitive Surgical Operations, Inc., Sunnyvale, CA (US)

(72) Inventors: Timothy D. Soper, San Jose, CA (US); Vincent Duindam, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 349 days.

(21) Appl. No.: 17/432,727

(22) PCT Filed: Feb. 24, 2020

(86) PCT No.: PCT/US2020/019465
§ 371 (c)(1),
(2) Date: Aug. 20, 2021

(87) PCT Pub. No.: WO2020/176400
PCT Pub. Date: Sep. 3, 2020

(65) Prior Publication Data
US 2022/0054202 A1 Feb. 24, 2022

Related U.S. Application Data

(60) Provisional application No. 62/810,623, filed on Feb. 26, 2019.

(51) Int. Cl.
*A61B 34/20* (2016.01)
*A61B 1/00* (2006.01)
(Continued)

(52) U.S. Cl.
CPC .......... *A61B 34/20* (2016.02); *A61B 1/00055* (2013.01); *A61B 1/005* (2013.01);
(Continued)

(58) Field of Classification Search
CPC ..... A61B 34/20; A61B 1/00055; A61B 1/005; A61B 34/10; A61B 34/25; A61B 2034/105; A61B 2034/2065
See application file for complete search history.

(56) References Cited

U.S. PATENT DOCUMENTS

| | | | |
|---|---|---|---|
| 6,389,187 B1 | 5/2002 | Greenaway et al. | |
| 7,316,681 B2 | 1/2008 | Madhani et al. | |

(Continued)

FOREIGN PATENT DOCUMENTS

| | | |
|---|---|---|
| WO | WO-2016133596 A1 | 8/2016 |
| WO | WO-2016164311 A1 | 10/2016 |

(Continued)

OTHER PUBLICATIONS

International Search Report and Written Opinion for Application No. PCT/US2020/019465, mailed on Jun. 9, 2020, 20 pages.

(Continued)

*Primary Examiner* — Rochelle D Turchen
(74) *Attorney, Agent, or Firm* — Haynes & Boone, LLP.

(57) ABSTRACT

A system may comprise a medical instrument, a tracking subsystem configured to receive position data from the medical instrument, and a control system communicatively coupled to the medical instrument and the tracking subsystem. The control system may be configured to perform operations including accessing a model of an anatomic structure of a patient and receiving an indication that the medical instrument has been delivered to a known anatomical landmark. The operations may also include collecting a plurality of measurement points of the anatomic structure along a measurement path extending from a measurement initiation position proximate the known anatomical landmark within the anatomic structure of the patient as the medical instrument moves along the measurement path. The operations may also include determining a location of the (Continued)

812 medical instrument relative to the anatomic structure and registering the collected plurality of measurement points to the model of the anatomic structure.

20 Claims, 15 Drawing Sheets

(51) Int. Cl.
|  |  |
|---|---|
| *A61B 1/005* | (2006.01) |
| *A61B 34/00* | (2016.01) |
| *A61B 34/10* | (2016.01) |

(52) U.S. Cl.
CPC .............. *A61B 34/10* (2016.02); *A61B 34/25* (2016.02); *A61B 2034/105* (2016.02); *A61B 2034/2065* (2016.02)

(56) References Cited

U.S. PATENT DOCUMENTS

| | | |
|---|---|---|
| 7,772,541 B2 | 8/2010 | Froggatt et al. |
| 8,900,131 B2 | 12/2014 | Chopra et al. |
| 9,259,274 B2 | 2/2016 | Prisco |
| 9,452,276 B2 | 9/2016 | Duindam et al. |
| 11,464,502 B2 * | 10/2022 | Tuma .................... A61B 90/39 |
| 2006/0013523 A1 | 1/2006 | Childers et al. |
| 2016/0008083 A1 * | 1/2016 | Kesten .................. A61B 5/062 |
| | | 600/424 |
| 2017/0084027 A1 | 3/2017 | Mintz et al. |
| 2018/0140361 A1 * | 5/2018 | Sinha .................... A61B 1/233 |

FOREIGN PATENT DOCUMENTS

| | | |
|---|---|---|
| WO | WO-2016191298 A1 | 12/2016 |
| WO | WO-2017030915 A1 | 2/2017 |
| WO | WO-2018085287 A1 | 5/2018 |
| WO | WO-2018144636 A1 | 8/2018 |
| WO | WO-2018144698 A1 | 8/2018 |
| WO | WO-2018195216 A1 | 10/2018 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2020/019465, mailed on Sep. 10, 2021, 11 pages.

* cited by examiner

500

| | |
|---|---|
| 502 | OBTAIN PRE-OPERATIVE OR INTRA-OPERATIVE IMAGING DATA OF A PATIENT ANATOMY |
| 504 | SEGMENT AN ANATOMICAL MODEL OF THE ANATOMY |
| 506 | COLLECT MEASUREMENT POINTS FROM THE PATIENT ANATOMY |
| 508 | OPTIONALLY, NOTIFY A USER OF COMPLETION OF THE COLLECTION OF THE MEASUREMENT POINTS |
| 510 | REGISTER THE MEASURED POINTS WITH THE MODEL OF THE PATIENT ANATOMY |

700

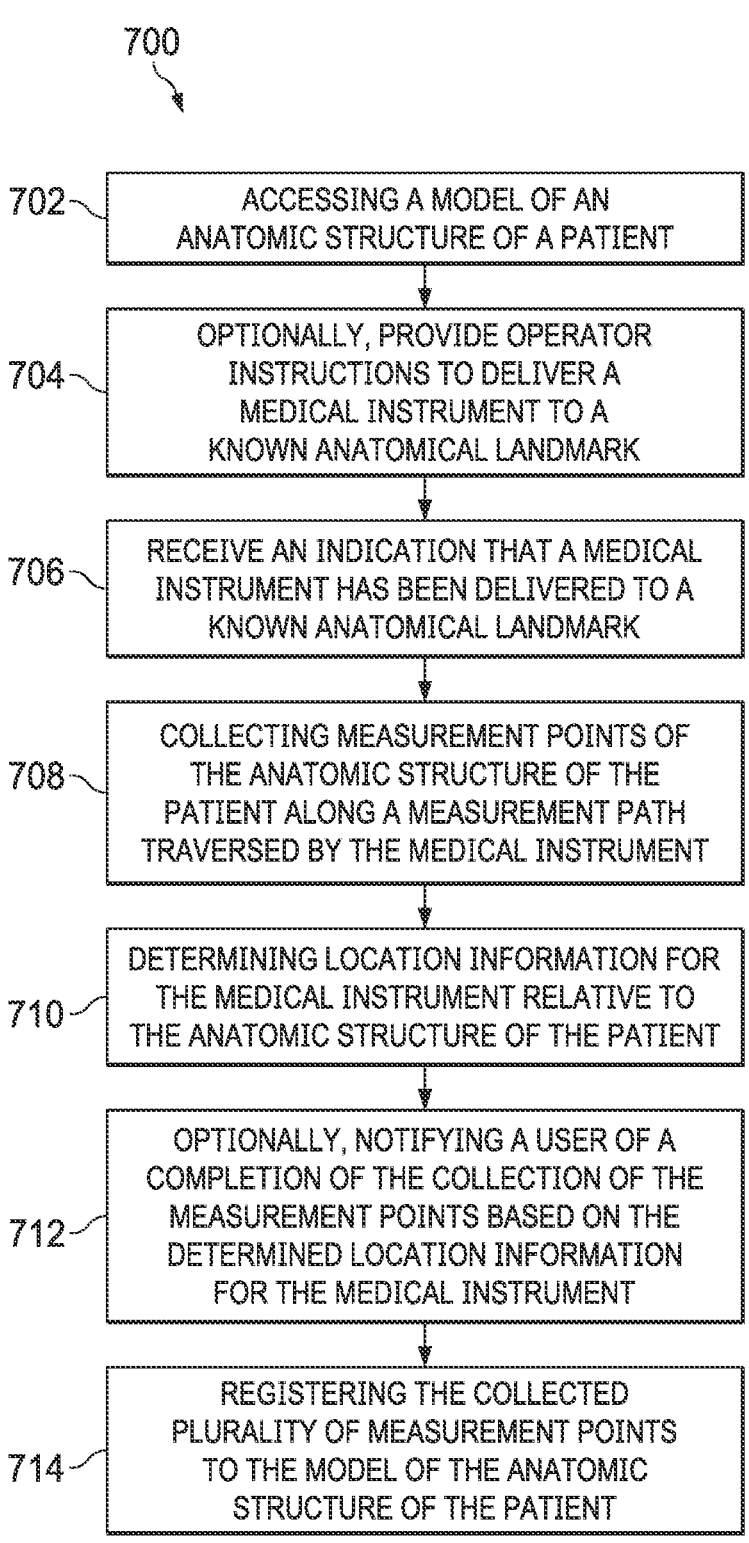

702 — ACCESSING A MODEL OF AN ANATOMIC STRUCTURE OF A PATIENT

704 — OPTIONALLY, PROVIDE OPERATOR INSTRUCTIONS TO DELIVER A MEDICAL INSTRUMENT TO A KNOWN ANATOMICAL LANDMARK

706 — RECEIVE AN INDICATION THAT A MEDICAL INSTRUMENT HAS BEEN DELIVERED TO A KNOWN ANATOMICAL LANDMARK

708 — COLLECTING MEASUREMENT POINTS OF THE ANATOMIC STRUCTURE OF THE PATIENT ALONG A MEASUREMENT PATH TRAVERSED BY THE MEDICAL INSTRUMENT

710 — DETERMINING LOCATION INFORMATION FOR THE MEDICAL INSTRUMENT RELATIVE TO THE ANATOMIC STRUCTURE OF THE PATIENT

712 — OPTIONALLY, NOTIFYING A USER OF A COMPLETION OF THE COLLECTION OF THE MEASUREMENT POINTS BASED ON THE DETERMINED LOCATION INFORMATION FOR THE MEDICAL INSTRUMENT

714 — REGISTERING THE COLLECTED PLURALITY OF MEASUREMENT POINTS TO THE MODEL OF THE ANATOMIC STRUCTURE OF THE PATIENT

Fig. 7

SYSTEMS AND METHODS FOR REGISTRATION OF PATIENT ANATOMY

CROSS-REFERENCE TO RELATED APPLICATIONS

This application is a U.S. National Stage patent application of International Patent Application No. PCT/US2020/019465 filed on Feb. 24, 2020, which claims priority to and the benefit of U.S. Provisional Application 62/810,623 filed Feb. 26, 2019, all of which are is incorporated by reference herein in their its entirety.

FIELD

The present disclosure is directed to systems and methods for conducting an image-guided procedure, and more particularly to systems and methods for semi-automatically registering real-time images and prior-time anatomic images during an image-guided procedure while requiring reduced operator input.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. However, to correlate the image-guided instruments to the images, an operator usually is required to manually move the image-guided instruments to specific locations within the anatomic systems and then notify a medical system that the image-guided instruments are located at the specified location prior to moving the image-guided instrument to another location within the anatomic systems to conduct the correlation, or registration process. This process may require substantial amounts of time and operator input to complete. Accordingly, it would be advantageous to provide a more efficient registration process for performing image-guided procedures.

SUMMARY

Embodiments of the invention are best summarized by the claims that follow the description.

Consistent with some embodiments, a system comprises a medical instrument, a tracking subsystem configured to receive position data from the medical instrument, and a control system communicatively coupled to the medical instrument and the tracking subsystem. The control system is configured to access a model of an anatomic structure of a patient and receive an indication that a medical instrument has been delivered to a known anatomical landmark within the anatomic structure of the patient. The control system is also configured to collect a plurality of measurement points of the anatomic structure of the patient along a measurement path extending from a measurement initiation position proximate the known anatomical landmark within the anatomic structure of the patient, as the medical instrument moves along the measurement path. The control system is further configured to determine a location of the medical instrument relative to the anatomic structure of the patient. Finally, the system is configured to register the collected plurality of measurement points to the model of the anatomic structure of the patient.

Consistent with some embodiments, a method comprises accessing a model of an anatomic structure of a patient and receiving an indication that a medical instrument has been delivered to a known anatomical landmark within the anatomic structure of the patient. The method also includes collecting a plurality of measurement points of the anatomic structure of the patient along a measurement path extending from a measurement initiation position proximate the known anatomical landmark within the anatomic structure of the patient as the medical instrument is moved along the measurement path. The method further includes determining a location of the medical instrument relative to the anatomic structure of the patient. Finally, the method includes registering the collected plurality of measurement points to the model of the anatomic structure of the patient.

Consistent with some embodiments, a non-transitory machine-readable medium comprising a plurality of machine readable instructions which, when executed by one or more processors, are adapted to cause the one or more processors to perform a method comprising accessing a model of an anatomic structure of a patient. The method also includes receiving an indication that a medical instrument has been delivered to a known anatomical landmark within the anatomic structure of the patient and collecting a plurality of measurement points of the anatomic structure of the patient along a measurement path extending from a measurement initiation position proximate the known anatomical landmark within the anatomic structure of the patient as the medical instrument is moved along the measurement path. The method further includes determining a location of the medical instrument relative to the anatomic structure of the patient. Finally, the method includes registering the collected plurality of measurement points to the model of the anatomic structure of the patient.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figures 2A, 2B:
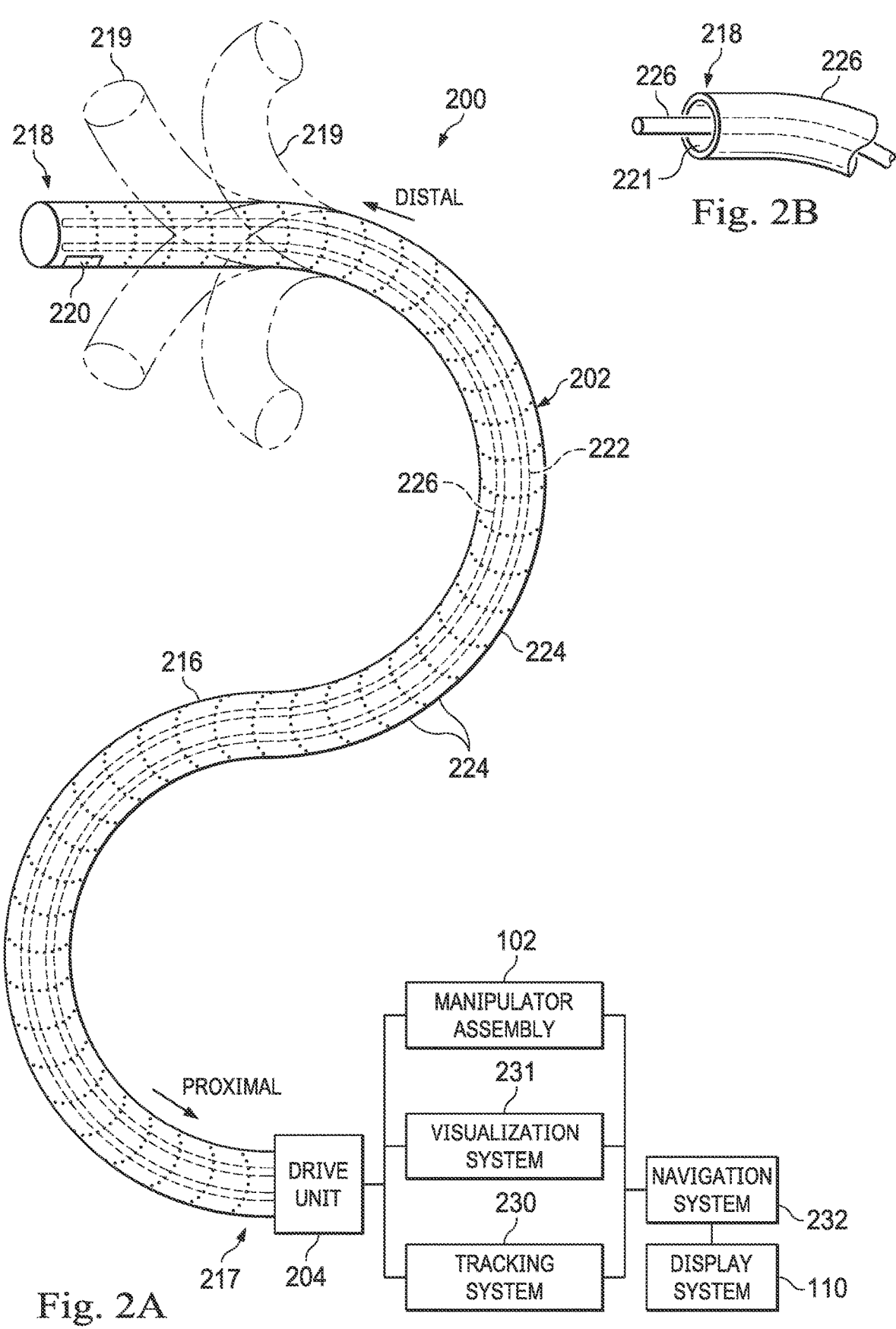
FIG. 2A is a simplified diagram of a medical instrument system according to some embodiments.
FIG. 2B is a simplified diagram of a medical instrument with an extended medical tool according to some embodiments.
Figure 3A:
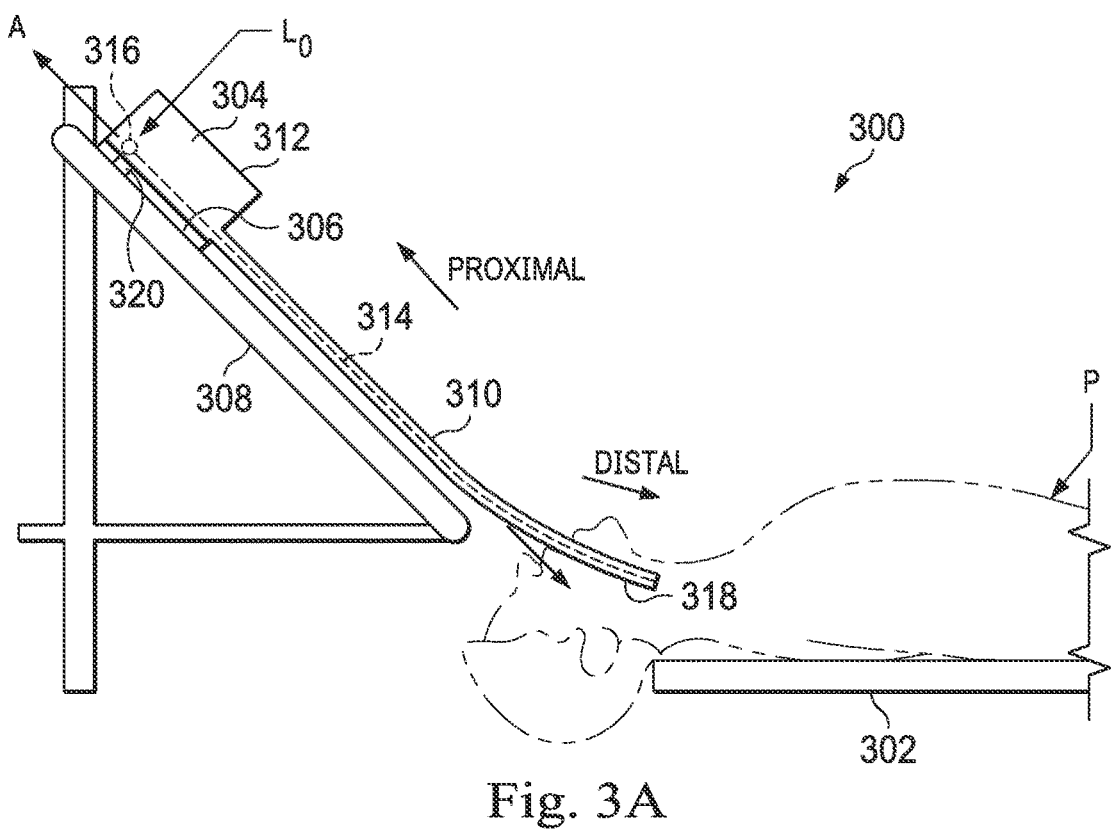
FIGS. 3A and 3B are simplified diagrams of side views of a patient coordinate space including a medical instrument mounted on an insertion assembly according to some embodiments.
Figure 3B:
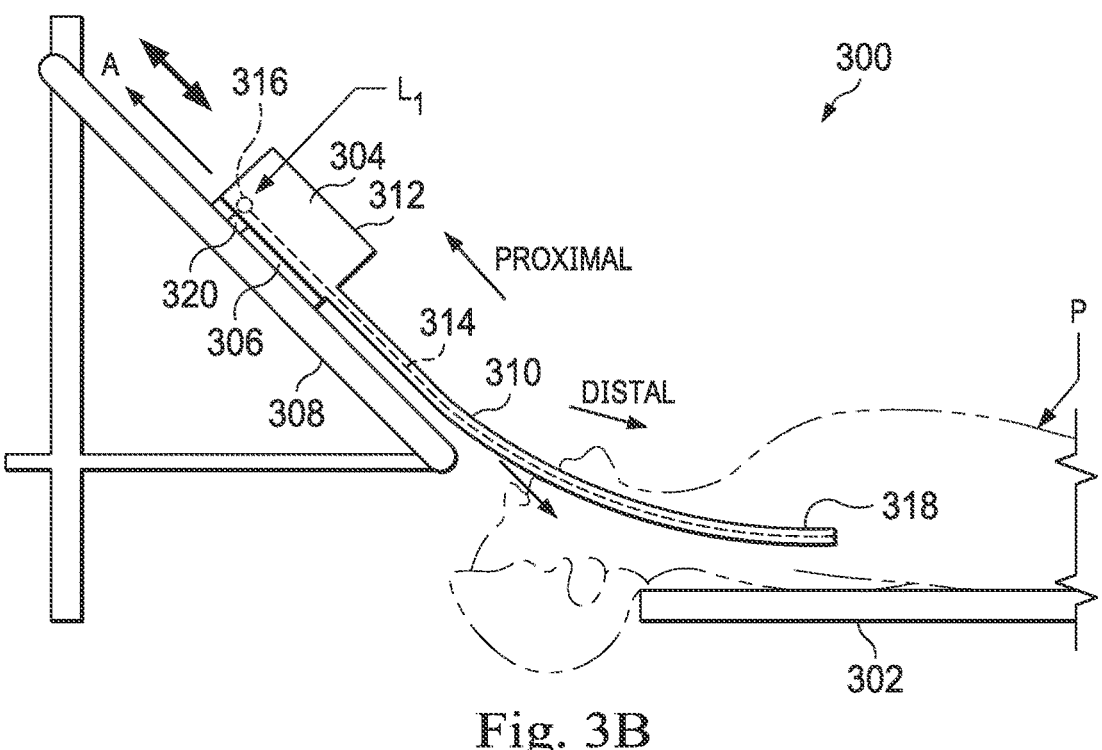
Figure 4A:
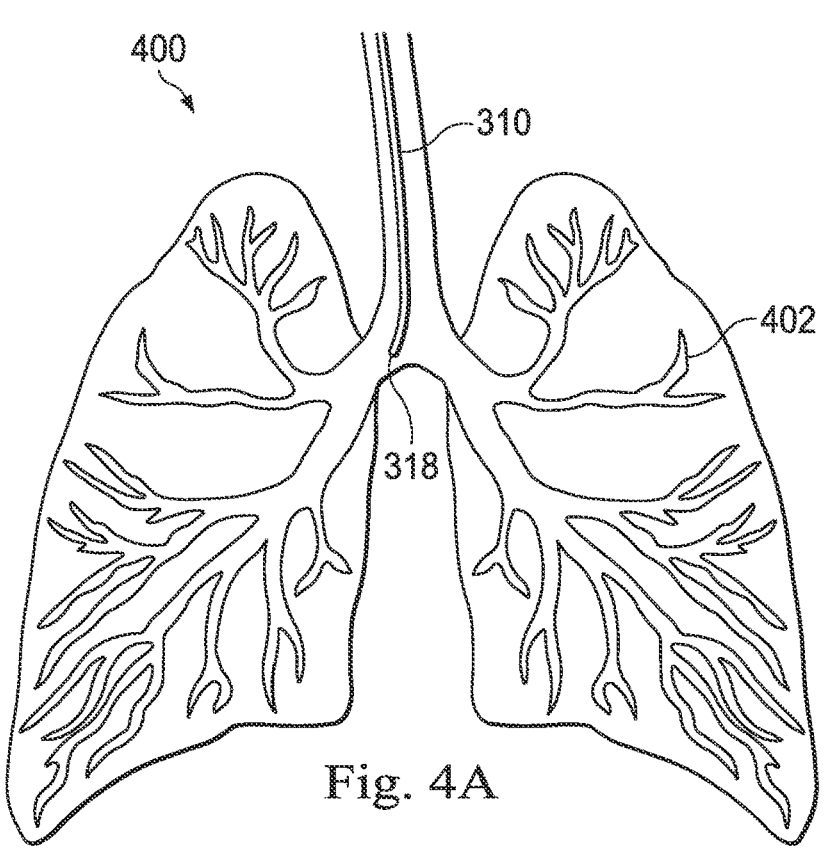
Figure 4B:
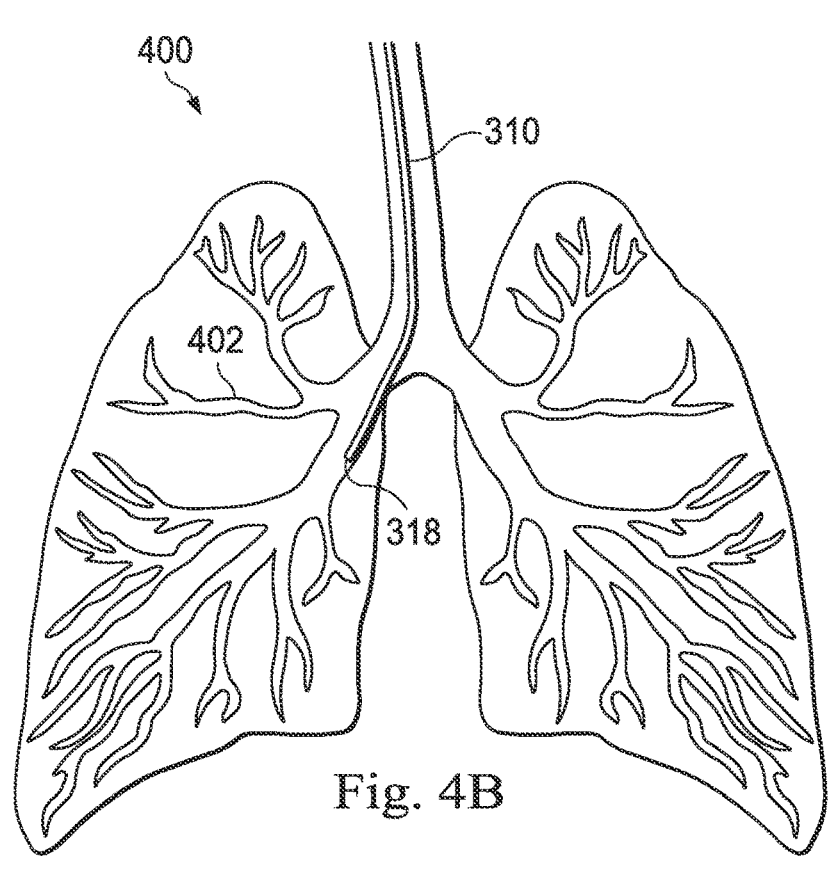
Figure 4C:
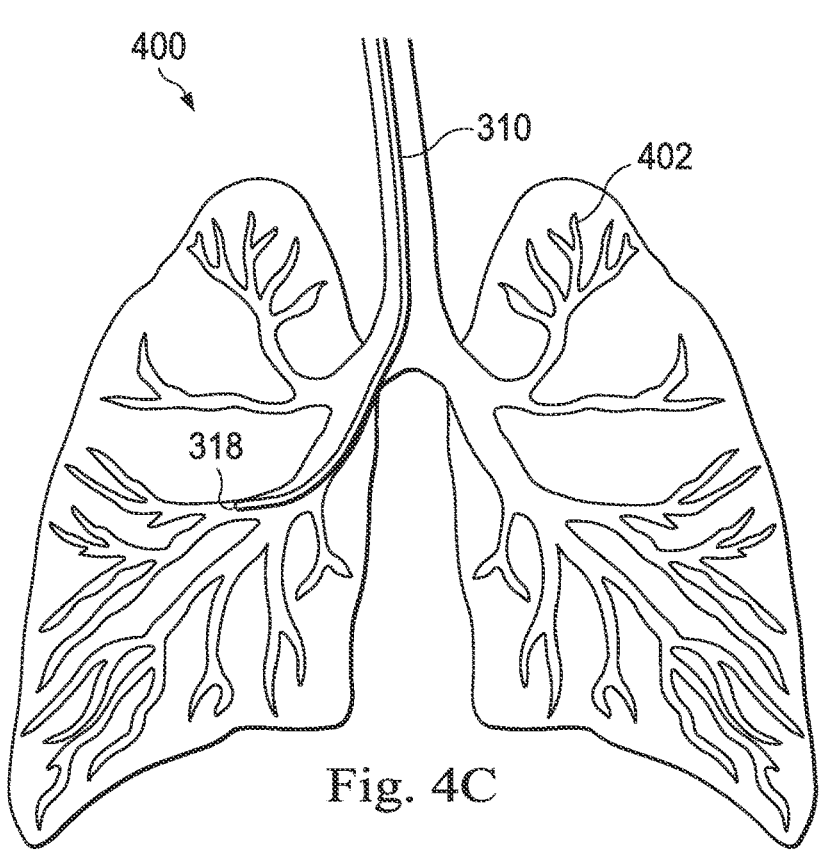
Figure 4D:
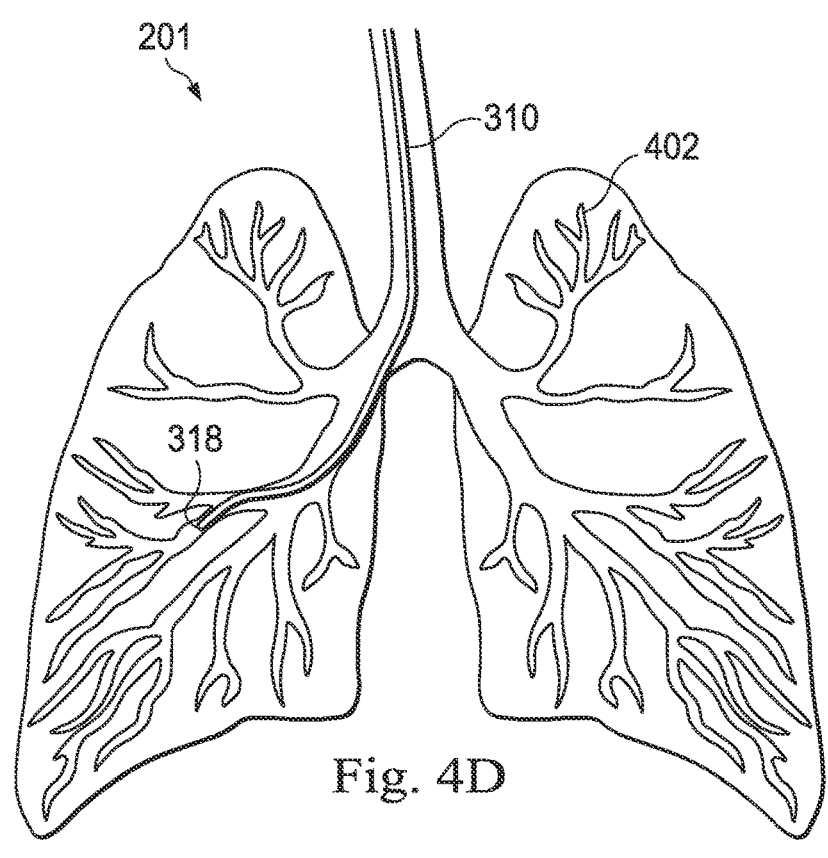

FIGS. 4A, 4B, 4C, and 4D illustrate the distal end of the medical instrument system of FIGS. 2, 3A, 3B, during insertion within a human lung according to some embodiments.

Figure 5:
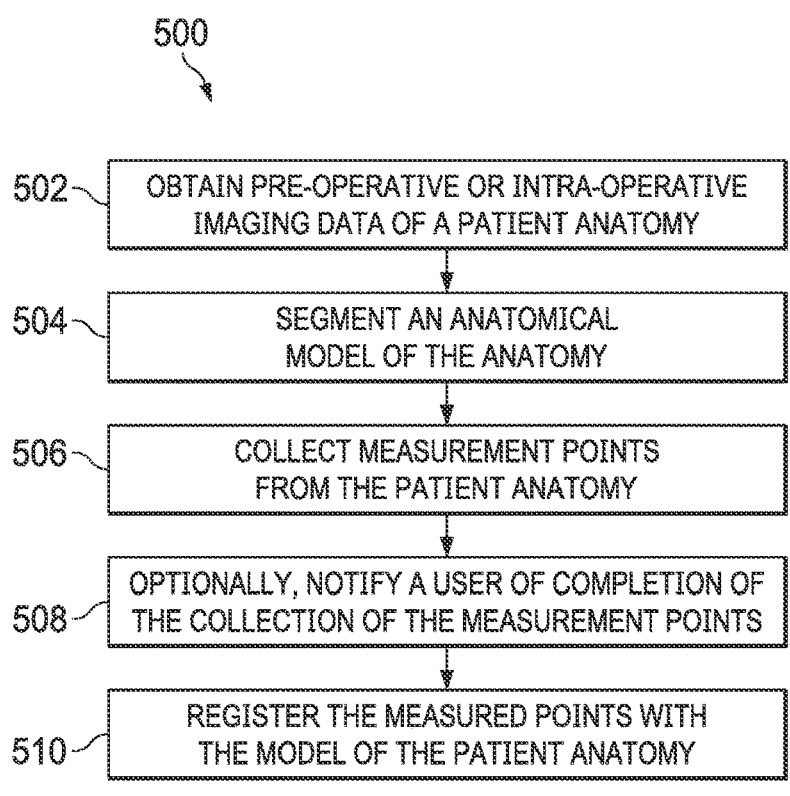

FIG. 5 is a flow chart illustrating a method of an image-guided surgical procedure or a portion thereof according to some embodiments.

Figure 6:
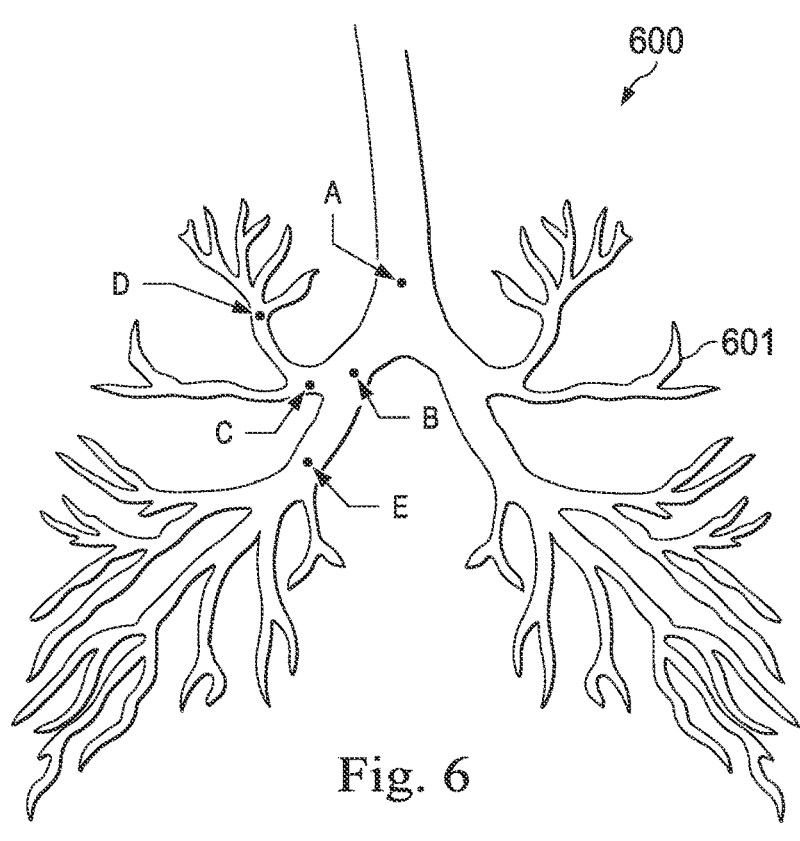

FIG. 6 illustrates an anatomic model of an anatomic region generated from preoperative or intraoperative image data.

FIG. 7 is a flow chart providing a method for performing a semi-automatic registration of a model of an anatomy of a patient P to the anatomy of the patient P as-present in a surgical environment according to some embodiments.

Figure 8:
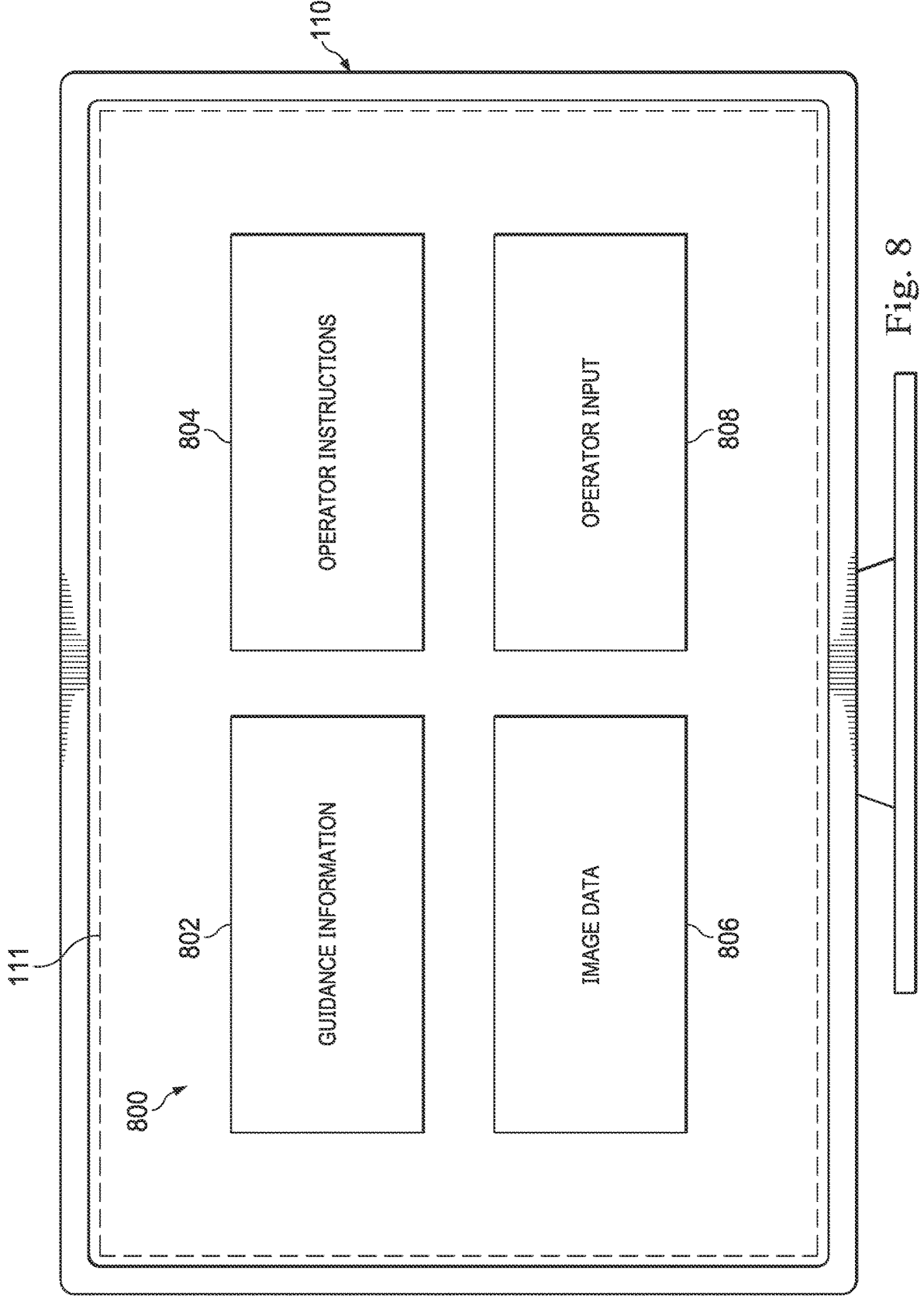

FIG. 8 illustrates a display system displaying, in a user interface included within the display system, a set of graphical information used to conduct a registration process between the model space and the patient space.

Figure 9:
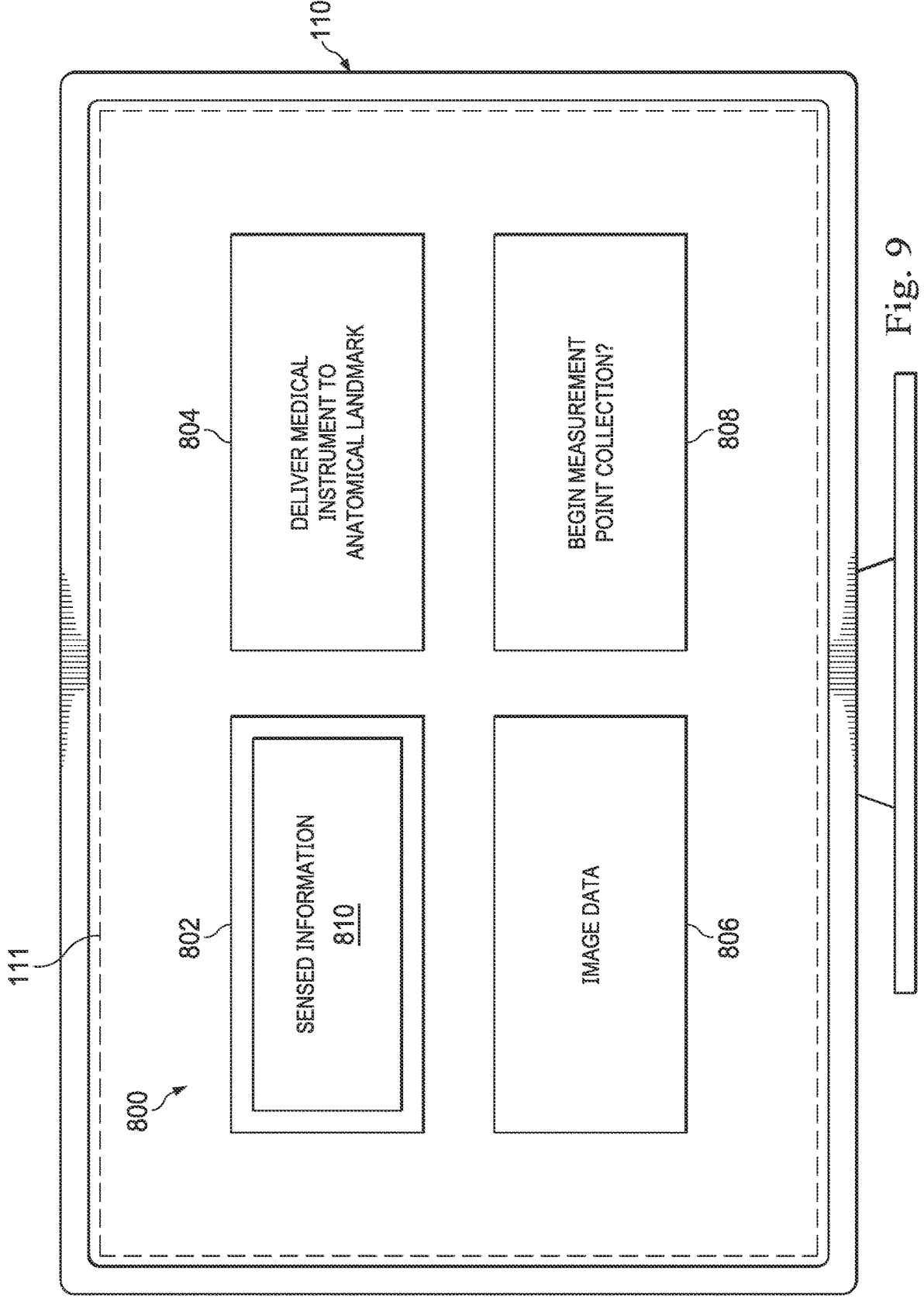

FIG. 9 illustrates the display system displaying, in the user interface, another set of graphical information used to conduct the registration process between the model space and the patient space.

Figure 10:
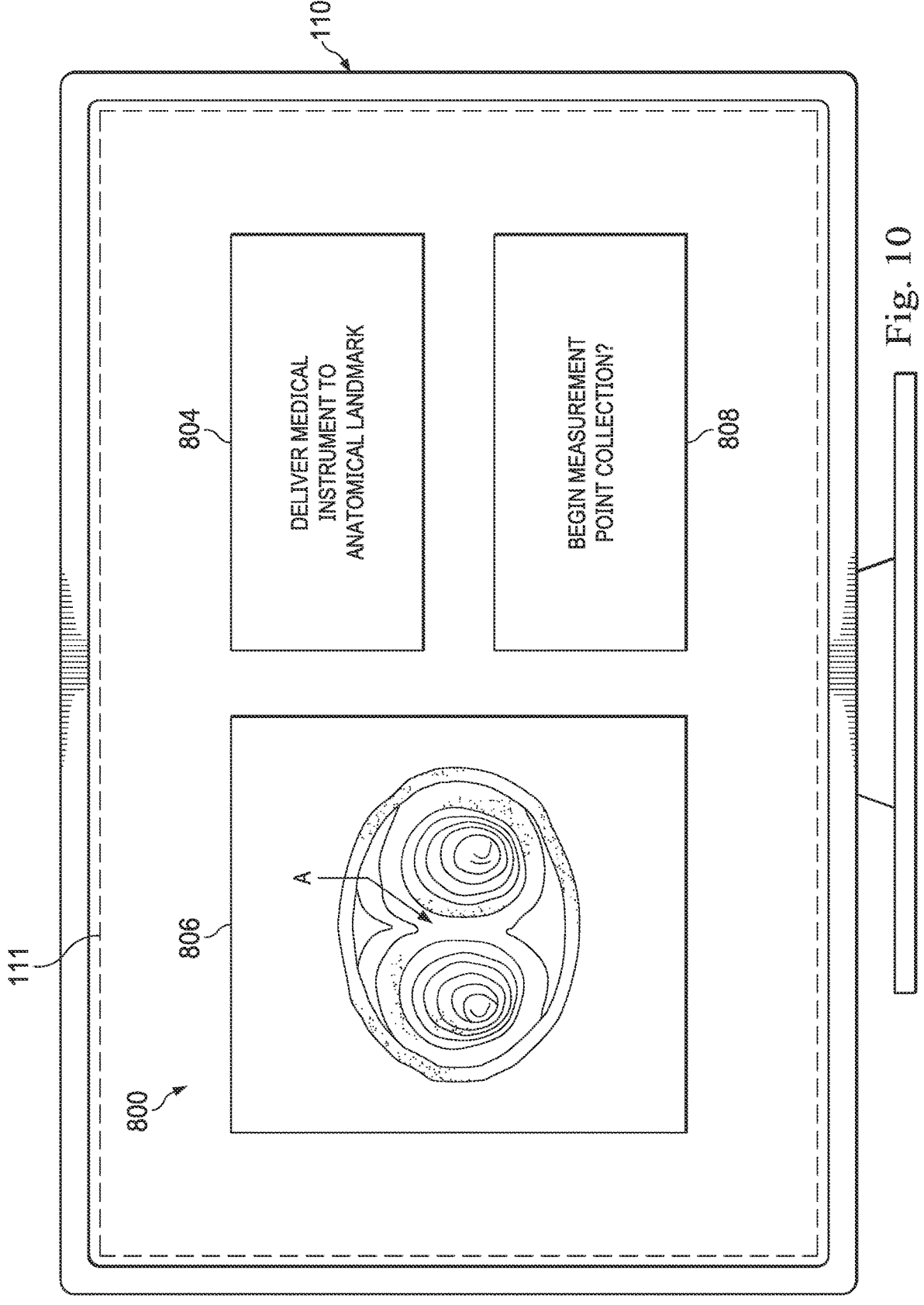

FIG. 10 illustrates the display system displaying, in the user interface, another set of graphical information used to conduct the registration process between the model space and the patient space.

Figure 11A:
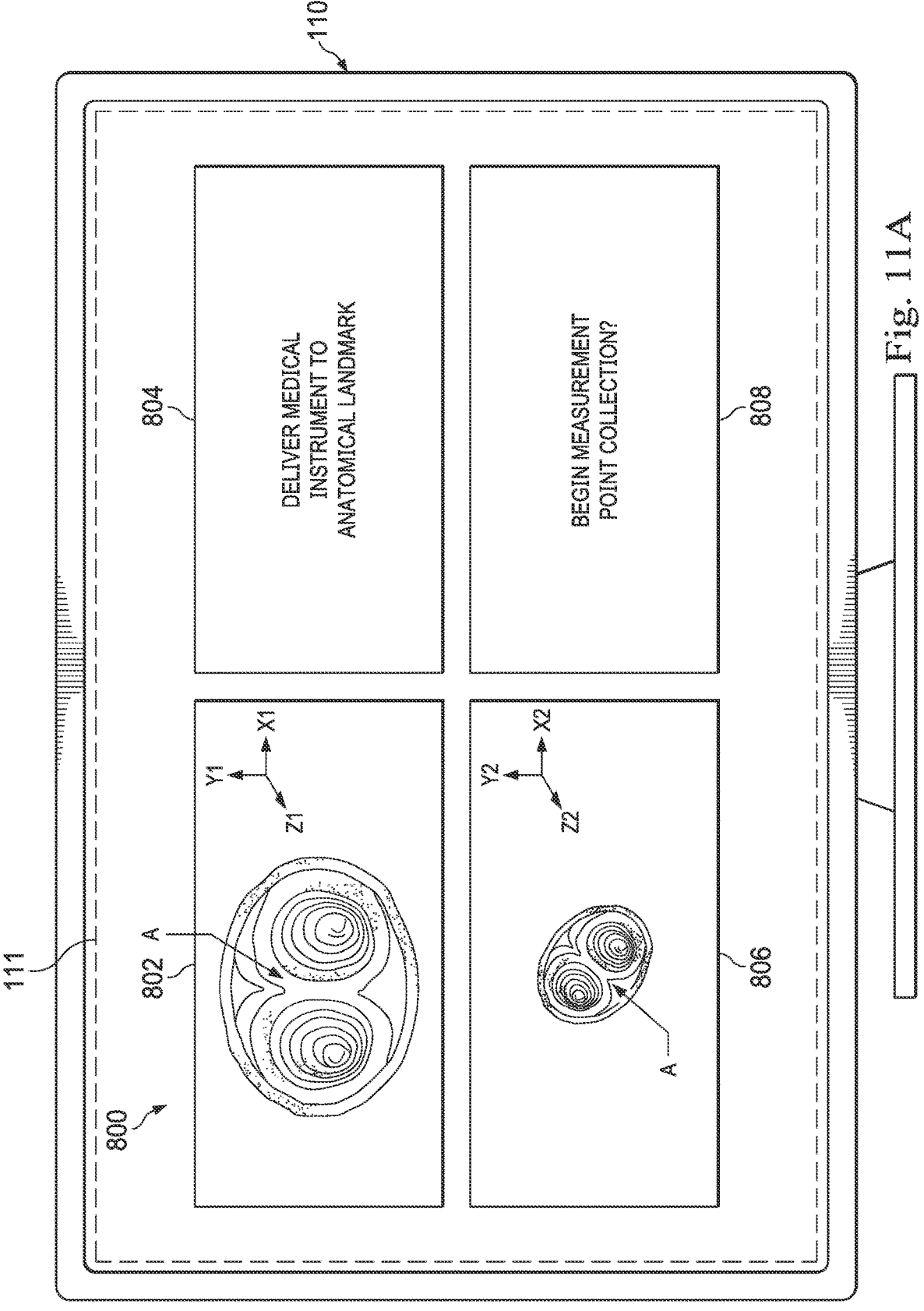
Figure 11B:
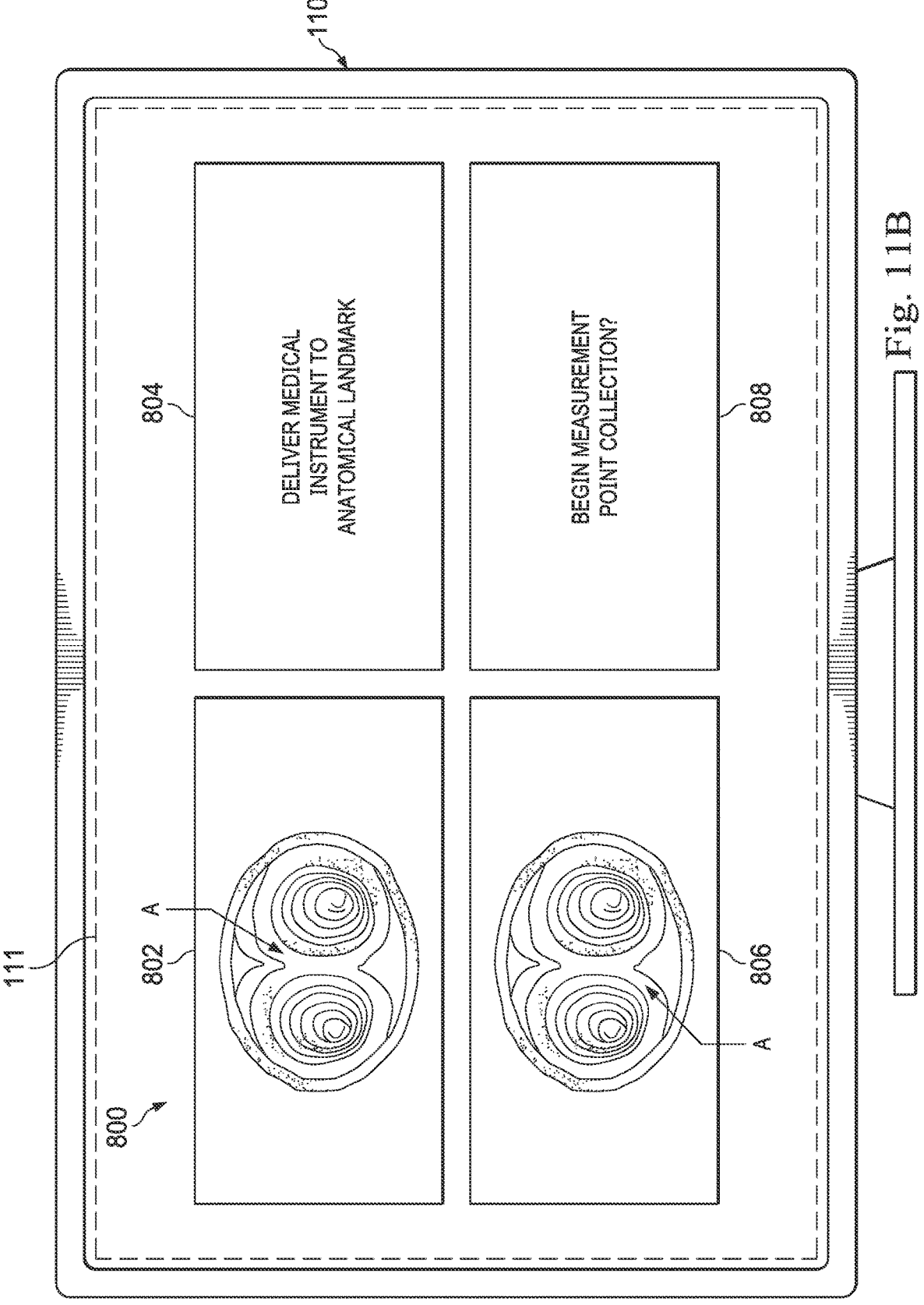

FIGS. 11A and 11B illustrate the display system displaying, in the user interface, another set of graphical information used to conduct the registration process between the model space and the patient space.

Figure 12:
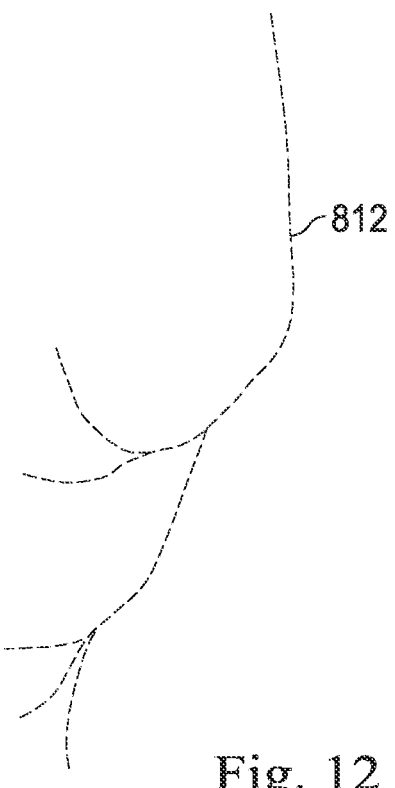

FIG. 12 illustrates a plurality measurement points gathered by an elongate device during the registration process between the model space and the patient space.

Figure 13:
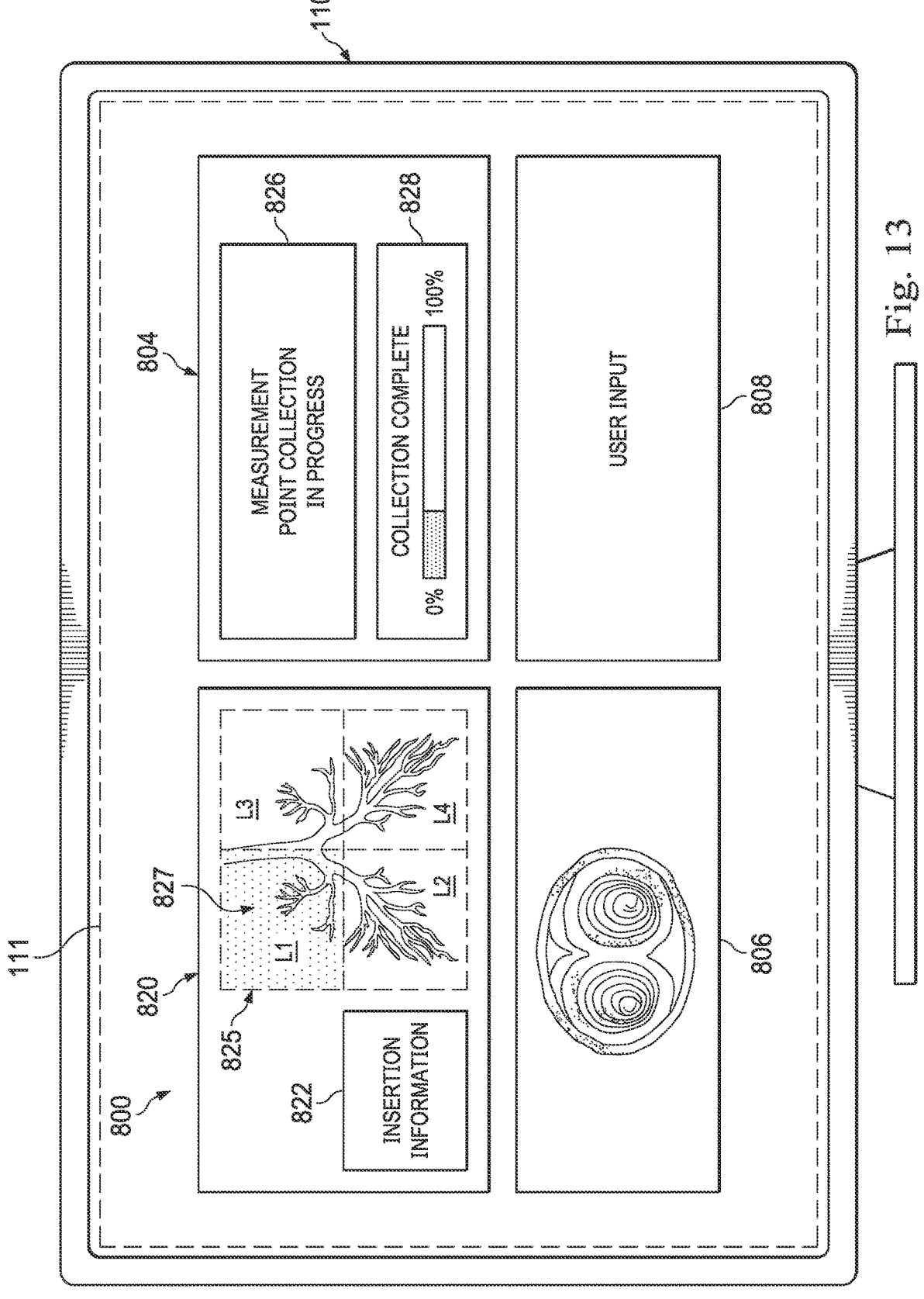

FIG. 13 illustrates the display system displaying, in the user interface, another set of graphical information used to conduct the registration process between the model space and the patient space.

Figure 14:
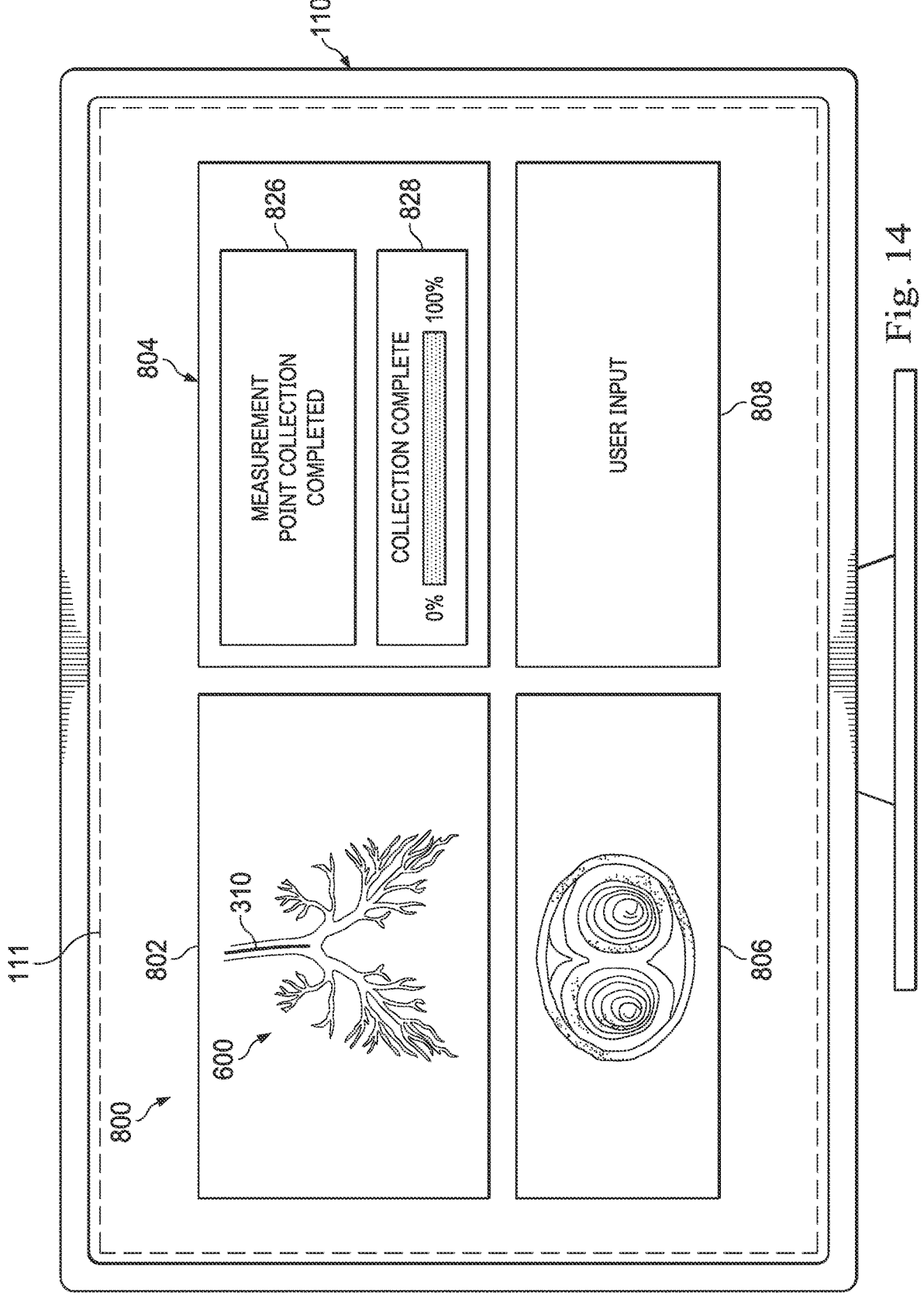

FIG. 14 illustrates the display system displaying, in the user interface, another set of graphical information used to conduct the registration process between the model space and the patient space.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Various embodiments of teleoperational medical systems including semi-automatic registration systems are described herein. In some embodiments, the systems may receive an indication that a medical instrument has been delivered proximate a known anatomical landmark within the anatomic structure of a patient to initiate a rough registration of the medical instrument to the anatomy of the patient. In some embodiments, the systems may include a medical instrument including an elongate flexible body and a sensor to collect a plurality of measured points within the anatomy of the patient. In some embodiments, the systems may collect a plurality of measurement points within the anatomy of the patient after rough registration has been initiated by delivering the medical instrument proximate the known anatomical landmark. In some embodiments, the systems may generate a virtual view that the user may use to complete the initial rough registration. While some embodiments are provided herein with respect to such procedures, any reference to medical or surgical instruments and medical or surgical methods is non-limiting. In some embodiments, the systems may be used for non-teleoperational procedures involving traditional manually operated medical instruments. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

Figure 1:
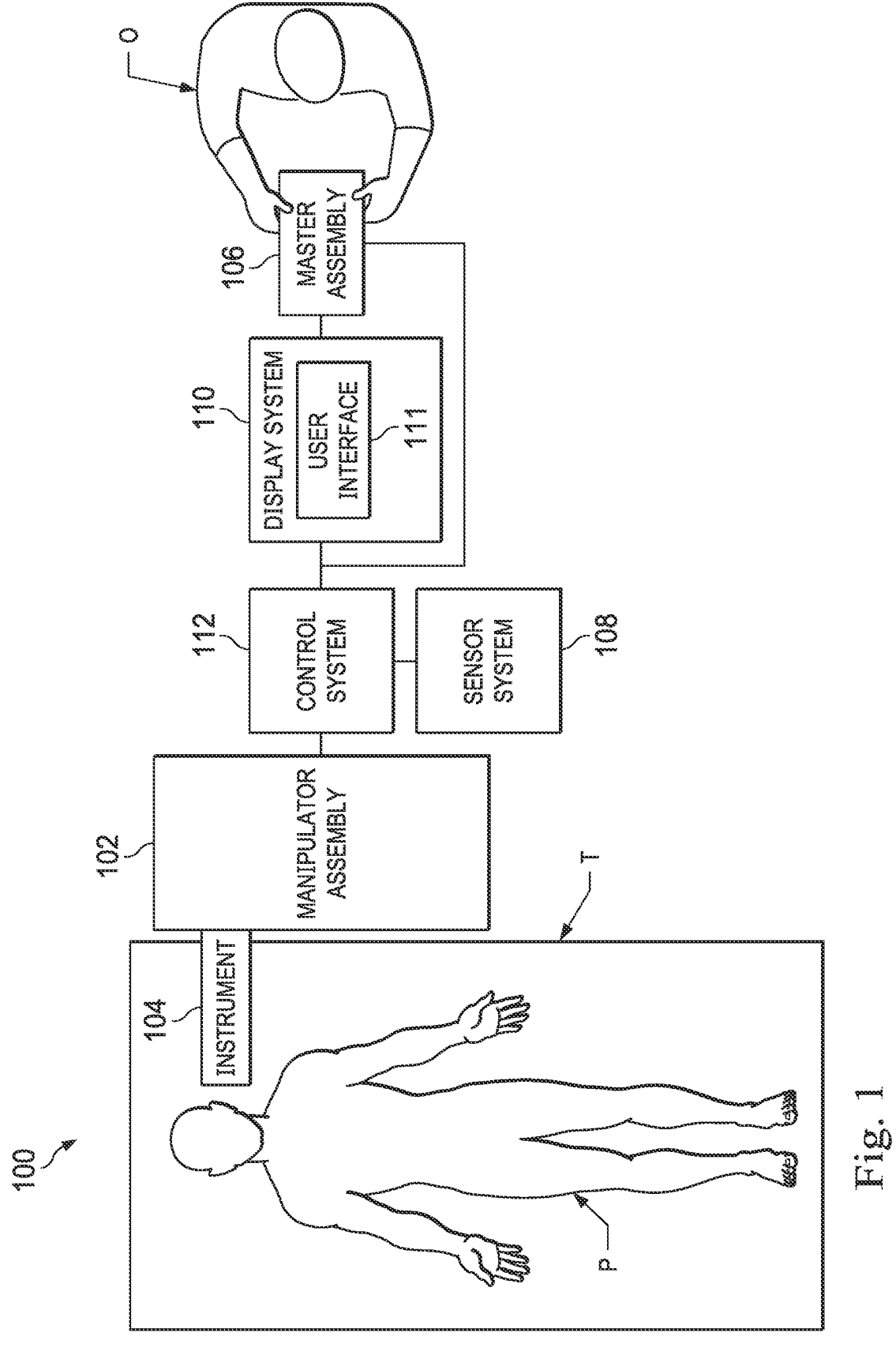
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting.

As shown in FIG. 1, medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or near an operating table T. A master assembly 106 allows an operator (e.g., a surgeon, a clinician, or a physician as illustrated in FIG. 1) O to view the interventional site and to control manipulator assembly 102.

Master assembly 106 may be located at an operator console which is usually located in the same room as operating table T, such as at the side of a surgical table on which patient P is located. However, it should be understood that the operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide the operator O a strong sense of directly controlling instruments 104 the control devices may be provided with the same degrees of freedom as the associated medical instrument 104. In this manner, the control devices provide the operator O with telepresence or the perception that the control devices are integral with medical instruments 104.

Manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so the operator O can control medical instrument 104 and master assembly 106 with the perception of telepresence.

In some embodiments, medical instrument 104 may and include a viewing scope assembly that records a concurrent or real-time image of a surgical site and provides the image to the operator or operator O through one or more displays of medical system 100, such as one or more displays of display system 110. The concurrent image may be, for example, a two or three-dimensional image captured by an endoscope positioned within the surgical site. In some embodiments, the visualization system includes endoscopic components that may be integrally or removably coupled to medical instrument 104. However, in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of the operator O. In this manner the operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity-based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist the operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist the operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface 111 by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth. IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include at least part of the virtual visualization system to provide navigation assistance to the operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three-dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more EM sensor, fiber optic sensors, and/or other sensors to register and display a medical implement together with preoperatively recorded surgical images, such as those from a virtual visualization system. For example, PCT Publication WO 2016/191298 (published Dec. 1, 2016) (disclosing "Systems and Methods of Registration for Image Guided Surgery"), which is incorporated by reference herein in its entirety, discloses such one system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end, or tip portion, 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220, such as an electromagnetic (EM) sensor system.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery." PCT Publication WO 2016/1033596 (filed May 20, 2016) (disclosing "Systems and Methods of Registration for Image Guided Surgery"), and PCT Publication WO 2016/164311 (filed Apr. 4, 2016) (disclosing "Systems and Methods of Registration Compensation in Image Guided Surgery"), which are incorporated by reference herein in their entirety.

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P that is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific phase in respiration and filtered such that the data is tagged and identified with that phase. In some embodiments, the phase during which data is collected may be inferred from physiological information collected from patient P. Within surgical environment 300, a point gathering instrument 304 is coupled to an instrument carriage 306. In some embodiments, the point gathering instrument 304 may include components of the medical instrument system 200 including, for example, the elongate device 202 and the drive unit 204. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310, or medical instrument, in multiple directions including yaw, pitch, and roll. Instrument carriage 306 or insertion stage 308 may include actuators, such as servomotors. (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position LU on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also, in this position, position measuring device 320 may be set to a zero and/or the other reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position L1 on the axis A. In this embodiment, a motion cycle of the elongate device 310 is defined as a single insertion of the elongate device 310 from a starting point within an entry orifice of the patient P to an end point further advanced into the anatomy of the patient P and a corresponding single retraction of the elongate device 310 from the end point to the starting point lying within the entry orifice of the patient P. Additionally, a plurality of motion cycles of the elongate device 310 may be completed during a procedure such as those that have been described above. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position L0. In some examples, position Lx may further be used as an indicator of the distance or insertion depth to which distal end 318 of elongate device 310 is inserted into the passageways of the anatomy of patient P.

FIGS. 4A, 4B, 4C, and 4D illustrate the advancement of elongate device 310 of FIGS. 3A and 3B through anatomic passageways 402 of the lungs 400 of the patient P of FIGS. 1 and 3A and 3B. These anatomic passageways 402 include the trachea and the bronchial tubes. As the elongate device 310 is advanced with the instrument carriage 306 moving along the insertion stage 308, the operator O may steer the distal end 318 of elongate device 310 to navigate through the anatomic passageways 402. In navigating through the anatomic passageways 402, elongate device 310 assumes a shape that may be measured by the shape sensor 314 extending within the elongate device 310.

FIG. 5 is a flowchart illustrating a general method 500 for use in an image-guided surgical procedure. The method 500 is illustrated in FIG. 5 as a set of operations or processes 502 through 510. Not all of the illustrated processes 502 through 510 may be performed in all embodiments of method 500. Additionally, one or more processes that are not expressly illustrated in FIG. 5 may be included before, after, in between, or as part of the processes 502 through 510. In some embodiments, one or more of the processes may be implemented, at least in part, in the form of executable code stored on non-transitory, tangible, machine-readable media that when run by one or more processors (e.g., the processors of control system 112) may cause the one or more processors to perform one or more of the processes.

At a process 502, pre-operative or intra-operative image data is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity-based information) images. For example, the image data may represent the human lungs 400 of FIGS. 4A-4D.

At a process 504, a computer system either operating alone or in combination with manual input is used to convert the recorded images into a segmented two-dimensional or three-dimensional composite representation or model of a partial or an entire anatomic organ or anatomic region. FIG. 6 illustrates an anatomic model of an anatomic region generated from pre-operative or intra-operative image data. In this example, FIG. 6 illustrates a segmented model 600 of the lungs 400 of FIGS. 4A-4D. Due to limitations in either the data or segmentation algorithm, the segmented model 600 may not include all of the passageways of interest present within the human lungs but includes some passageways 601. For example, relatively narrow and/or distal passageways of the lungs may not be fully included in the segmented model 600. The segmented model 600 may be a three-dimensional model, such as a mesh model, linkage model, or another suitable model defining the interior lumens or passageways of the lungs. In general, the model serves as a spatial template of the airway geometry within the pre-operative or intra-operative reference frame. The composite representation and the image data set describe the various locations and shapes of the passageways and their connectivity and may omit undesired portions of the anatomy included in the pre-operative or intra-operative image data. In some embodiments, the model 600 may include specifically desired features, such as a suspected tumor, lesion, or other tissue portion of interest.

During the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image, like the model 600. To represent the model, the segmentation process may delineate sets of voxels representing the target anatomy and then apply a function, such as marching cube function, to generate a 3D surface that encloses the voxels. The model may be made by generating a mesh, volume, or voxel map. This model may be shown in the display system 110 to aid the operator O in visualizing the anatomy, such as the interior passageways of the lungs.

As shown in FIG. 6, the model 600 includes several branch points, including the branch points A, B, C, D, and E. The branch point A, for example, may represent the point in the model 600 at which the trachea divides into the left and right principal bronchi. Within the right principal bronchus, a branch point B may represent the branching point in the model 600 between the right upper lobe and the right lower lobe. Similarly, secondary bronchi are identified by the branch points C and D in the right upper lobe and by the branch point E in the right lower lobe.

Returning to FIG. 5, at a process 506, a plurality of measurement points may be collected from the patient anatomy that correspond to the anatomical model, as described with reference to FIGS. 3A-B, 4A-D, and as will be described further herein. The measurement points may be generated by advancing an elongate device through anatomy and/or to landmarks in the anatomy and beyond, while measuring the position of a distal end of the elongate device or pose of the elongate device using a sensor system (e.g., the sensor system 108) while the control system (e.g., the control system 112) monitors the collection of the measurement points to determine when an adequate amount of data in the form of the measurement points have been collected. The measured points are associated with a patient space and may also be referred to as patient space points.

At a process 508, optionally, one or more processors (e.g., the processors of control system 112) may notify the user of completion of the collection of the measurement points using, for example, a display (e.g., display system 110). The notification to the user may include a visual alert on the display system 110 that notifies the user, for example, of a completed survey of a sub-region of the patient anatomy or a percentage completion of the measurement point collection process.

At a process 510, the anatomic model data of a model space is registered to the patient anatomy of a patient space (or vice versa) after the completion of the measurement point collection process 508 and prior to or during an image-guided surgical procedure on the patient. Generally, registration involves the matching of the collected plurality of measurement points to points in the model 600, through the use of rigid and/or non-rigid transforms. A point set registration method (e.g., iterative closest point (ICP) technique) may also be used in registration processes within the scope of this disclosure. Such a point set registration method may generate a transformation that aligns the measured points (also referred to as a measured point set) and the model points (also referred to as the measurement point set).

In various embodiments, the quality of the registration may depend on various factors, including for example, the numbers of the measured points and/or model points, the density of the measured points and/or model points, the distribution of the measured points and/or model points relative to a region of interest, measurement errors associated with the measured points and/or model points, and deformation of the patient anatomy associated with the measured points and/or model points. In at least some instances, to facilitate improving the quality of the registration, the notification to the user of completion of the collection of the measurement points is based on at least one of the above-listed factors.

FIG. 7 illustrates a method 70) of operating at least a portion of the teleoperated medical system 100 for registering a model space, for example the model 600, to the patient space, for example the anatomic structures of the patient P, in a surgical environment according to some embodiments. FIGS. 8, 9, 10, 11A, 11B, 13, and 14 illustrate the display system 110 displaying, in a user interface 111 included within the display system, a set of graphical information used to conduct a registration process between the model space and the patient space, as will be described further herein. The method 700 is illustrated as a set of operations or processes. The method 700 facilitates registration of the anatomic model 600 to the anatomic structures of the patient P in the surgical environment. Specifically, the operator O is able to advance the elongate device 310 (also referred to as the elongate device 310) throughout the anatomical structures of the patient P to perform a preliminary registration and a comprehensive registration. As will be described, operator guidance may be provided during the preliminary registration and during the instrument survey to collect measured points for the comprehensive registration. This user guidance may increase the efficiency and accuracy of the registration process.

Not all of the illustrated processes may be performed in all embodiments of method 700. Additionally, one or more processes that are not expressly illustrated in FIG. 7 may be included before, after, in between, or as part of the processes. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes may be performed by a control system (e.g., control system 112).

To guide the registration method 700, a set of graphical information 800 may be displayed in the user interface 111, as shown in FIG. 8. The set of graphical information 800 may include guidance information 802 which may include information from the model 600 and/or information from a medical instrument such as elongate device 310. The set of graphical information 800 may also include operator instructions 804 which may include text or illustrations to instruct users about the steps of the registration process, deliver operator commands, or to provide operator feedback about operator actions. The set of graphical information 800 may also include image data 806 such as real-time image data generated from an imaging device (e.g., a stereoscopic camera) in the elongate device 310. The set of set of graphical information 800 may also include an operator input portion 808 which may be, for example, a touch responsive button that allows an operator to indicate confirmation, start a process, stop a process, or provide other commands to the control system 112. Alternatively, user input may be provided through any of a variety of peripheral devices includes a trackball, hand controllers, voice controllers, eye tracking systems, or other operator gesture recognition devices. In various embodiments, any of the information 802-808 may be suppressed or otherwise not displayed on the user interface during some processes of the method 700.

The method 700 includes a process 702 in which an anatomic model (e.g., model 600) may be accessed from a computer memory associated with the control system 112 or may be otherwise generated by the control system 112. Optionally, portions of the model 600 may be displayed as guidance information 802, as will be described.

At an optional process 704, operator instructions 804 are displayed instructing an operator to, for example, deliver a medical instrument to an anatomic landmark within the anatomy of the patient P to initiate the registration process. In this embodiment of the method, the medical instrument may correspond to the elongate device 310, but in other embodiments, the method may be performed using another type of medical instrument 104. The elongate device 310 may carry an imaging device (e.g., a stereoscopic camera of an imaging probe) for generating real-time endoscopic image data of the patient anatomy. In some embodiments, instructions may be given to the operator in the form of an audible alert, a vibratory alert, or any other type of notification that indicates to the operator that the control system 112 is awaiting delivery of the elongate device 310 to an anatomical landmark to initiate the registration process.

In some embodiments, the anatomical landmark may be the branch point A at the carina of the trachea where the trachea divides into left and right principal bronchi. Although the method 700 will reference the know anatomical landmark of branch point A, in other embodiments, the operator may be instructed to deliver the medical instrument to other anatomical landmarks.

With reference to FIG. 9, in some embodiments, the delivery of the medical instrument to the anatomic landmark at the branch point A may be guided by the display of sensed information 810. Sensed information 810 may include information about the insertion depth, position, orientation, or shape of the medical instrument received, for example, from insertion sensors, position sensors, shape sensors, or fluoroscopic images of the medical instrument. The sensed information 810 may be used in combination with known general anatomical information or from the patient model 600 such as anatomical dimensions including airway lengths, diameters, and angular orientations.

With reference to FIG. 10, in some embodiments, the delivery of the medical instrument to the anatomic landmark at the branch point A may be guided by the display of the image data 806. The image data 806 may be real-time image data generated from an imaging device (e.g., a stereoscopic camera) in the elongate device 310. The anatomic landmark at branch point A may have distinctive characteristics such as shape, dimensions, and coloring that are identifiable by a viewer of the image data 806 presented on the user interface 111. When the distinctive features associated with the anatomic landmark at branch point A become visible in the image data 806, the operator may recognize that the distal end of the medical instrument has been delivered to the branch point A.

With reference to FIGS. 1A and 1B, in some embodiments, the delivery of the medical instrument to the anatomic landmark at the branch point A may be guided by the display of the image data 806 together with guidance information 802 in the form of an image of a virtual view the anatomic landmark at branch point A generated from the model 600. The image of the branch point A from the model 600 may be selected, for example, by a user or by the control system 112 based upon identifying criteria associated with the branch point A and the use of graphic analysis and recognition techniques. The guidance information 802 in the form of the virtual view of the anatomical landmark branch point A is generated from a virtual endoscopic perspective. The guidance information 802 in the form of the virtual view may have a coordinate reference frame X1, Y1, Z1 associated with the model 600. The image data 806 may be a live or real-time view generated from an imaging device (e.g., a stereoscopic camera) in the elongate device 310. The image data 806 in the form of the real-time view may have a coordinate reference frame X2, Y2, Z2 associated with a distal end of the elongate device 310. Using the guidance information 802 in the form of the virtual view of the branch point A generated from the model 600, the elongate device 310 may be inserted, retracted, rotated, pivoted, or otherwise moved until the image data 806 aligns or matches with the position and orientation of the guidance information 802 in the form of the virtual view from the model 600. The movement of the elongate device 310 may be controlled manually or teleoperatively by the operator or may be controlled by matching operations of the control system 112. As shown in FIG. 11A, the image data 806 from the elongate device 310 may show the branch point A farther away and at an angle of rotation different from the branch point A in the guidance information 802 in the form of the virtual view. As shown in FIG. 11B, the elongate device 310 may be rotated and advanced into the airway until the image data 806 closely matches the virtual view 802 as determined by operator observation or by a matching operation of the control system 112 using graphic analysis and recognition techniques. In alternative embodiments, the guidance information 802 in the form of the virtual view may be adjusted to match the image data 806. In alternative embodiments, the virtual view and the real-time view may be superimposed on each other to facilitate the matching.

At a process 706, an indication is received at the control system 112 that the elongate device 310 has been delivered to the location proximate to the known anatomical landmark at branch point A. The received indication may trigger the control system 112 to perform a rough or preliminary registration of the coordinate system X1, Y1, Z1 of the model 600 and coordinate system X2, Y2, Z2 of the distal end of the elongate device 310 and/or trigger the measurement point collection process. In some embodiments, the indication may be received from the operator. For example, the operator may provide the indication by selecting the operator input portion 808 "BEGIN MEASUREMENT POINT COLLECTION?" displayed on the user interface 111. In some embodiments, the operator may indicate that the distal tip 318 has been delivered proximate the known anatomical landmark by any method, including speaking a command, inputting a code, performing a gesture, or any other method that facilitates operation of the teleoperated medical system 100 as described herein. In some embodiments, the indication that the elongate device has been delivered to the known anatomical landmark may be determined, without further user input, by a matching operation of the control system 112 using graphic analysis and recognition techniques. In this regard, vision recognition may be performed based upon image data received from an imaging device of the elongate device 310. The vision recognition may be performed, for example, by control system 112 identifying the known anatomical landmark in the image data and automatically generating the indication that the elongate device has been delivered to the known anatomical landmark. In some embodiments, the indication that the elongate device 310 has been delivered to the known anatomical landmark within the anatomic structure of the patient P is received from the elongate device 310 and does not require a user input to progress to a next step in the process. For example, determined from insertion information indicating an insertion depth of the elongate device 310. For example, insertion information may be determined by tracking system 230 from insertion sensors in the elongate device 310 or on the manipulator assembly 102. Additionally, or alternatively, insertion information may be determined from position and/or shape sensors in the elongate device 310. In additional embodiments, the notification of the delivery of the elongate device 310 proximate the known anatomical landmark P may be received by any method that facilitates operation of the teleoperational system 100 as described herein.

At a process 708 and with reference to FIG. 12, the elongate device 310 may be used as a point gathering device to collect a plurality of measurement points 812 as the instrument surveys or traverses a measurement path through the anatomic structure of the patient P. The measurement points 812 may be identified with position data in the coordinate reference frame X2, Y2, Z2 associated with a distal end of the elongate device 310. In some additional embodiments, the elongate device 310 includes a shape sensor, and the plurality of measurement points 812 are collected as the elongate device surveys the anatomic structure of the patient P by interrogating the shape of the shape sensor, as has been described herein. In additional or alternative embodiments, the plurality of measurement points 812 may be collected using at least one of an imaging probe, an EM sensor, and/or any other sensors coupled to the elongate device 310. The process 708 may be initiated automatically in response to the indication that that the elongate device 310 has been delivered to the known anatomical landmark.

Additionally, for each measurement point 812, the preliminary registration computed from process 706 may be updated or refined. Or alternatively, the preliminary registration may be updated after collecting a plurality of measurement points 812, after inserting the elongate device 310 a predetermined distance, or after driving the elongate device 310 into a predetermined anatomical region of the anatomic structure of the patient P.

At a process 710, location information for the elongate device 310 is determined relative to the anatomic structure of the patient P. For example, and with reference to FIG. 13, location information 820 may be determined from insertion information 822 indicating an insertion depth of the elongate device 310. For example, insertion information 822 may be determined from insertion sensors in the elongate device 310 or on the manipulator assembly 102. Additionally, or alternatively, insertion information 822 may be determined from position and/or shape sensors in the elongate device 310. In some embodiments insertion depth may be measured relative to a known anatomic landmark such as branch point A at the main carina of the lung.

The location information 820 may also include anatomical region information 825. In this embodiment, the anatomical region information 825 may indicate the lobe of a lung in which the elongate device 310 has collected the measurement points 812. In this embodiment, the anatomical region information 825 may include an anatomic model map 827 associated with the model 600 or with a generalized map of airway passages in a human lung. The anatomic model map 827 may include a first region L1 corresponding to an upper right lobe region, a second region L2 corresponding to a lower right lobe region, a third region L3 corresponding to an upper left lobe region, and fourth region L4 corresponding to a lower left lobe region. In other embodiments, the fewer or more regions may be associated with the patient anatomy. In this embodiment, the location information 820 may be displayed on the user interface 111. In alternative embodiments, some or all of the location information 820 may be used for making determinations by the control system 112 without display on the user interface 111.

Based on the insertion information 822, the preliminary registration generated at the end of the process 706, and optionally, the position or shape sensor data from the elongate device 310, the region L1-L4 in which the elongate device 310 or the distal end portion of the elongate device 310 is located may be determined. Surveying of the region in which the elongate device 310 is located may continue until a collection threshold is reached. In some embodiments, the collection threshold may correspond to a depth threshold. A depth threshold may be a predetermined minimum measured insertion depth for the elongate device 310 in the region that indicates that the instrument has traversed a sufficient insertion distance into the region. In other embodiments, the collection threshold may correspond to a quantity threshold. A quantity threshold may be a predetermined minimum number of measurement points 812 collected for a region. In other embodiments, the collection threshold may correspond to a time threshold. A time threshold may correspond to an amount of time that the instrument 310 has been traveling along the measurement path in the region within the anatomy of the patient P. In some additional embodiments, the completion of the collection of the plurality of measurement points 812 for a region may be determined by any method that facilitates the operation of the teleoperational medical system 100 as described herein.

When the collection threshold has been reached for the region, the control system 112 may prompt the operator to survey a different region. The processes 708 and 710 of collecting measurement points and determining the location information for the medical instrument may be repeated for multiple regions.

For example, the insertion information 822 and the preliminary registration may indicate that the distal end of the elongate device 310 is located in the region L1 corresponding to the upper right lobe of the patient lung. Collection of measurement points 812 may continue in the region L1 with insertion of the elongate device 310 into and out of one or more passageways in the region L1 until a collection threshold is reached indicating that the medical instrument has been inserted to a sufficient depth or indicating that a sufficient number of measurement points 812 have been gathered in the region L1.

At an optional process 712, after the collection threshold has been reached, a notification may be provided to alert the operator that the collection threshold has been reached for the region. Based on the notification or on further instructions, the operator may begin surveying another region. The notification to the operator may be provided in the form of a textual notice in the operator instruction 804. Additionally or alternatively, the notification to the operator may be provided graphically by changing an appearance (e.g., a color or texture) of the completed region in the anatomical region information 825. For example, as shown in FIG. 13A, the region L1 may be shaded to indicate that the collection threshold has been reached for region L1. This shading may prompt the operator to begin surveying and collecting measurement points in another region such as region L2. In various embodiments, the operator instructions 804 may also or alternatively provide notifications 826 regarding the status of the measurement point collection. In various embodiments, the operator instructions 804 may also include a visual representation of a progression towards completion of the collection of the plurality of measurement progression in a display box 828. The measurement progression display box 828 is a visual representation of a percent completion of the process of collecting the measurement points 812, ranging from 0 percent (e.g., at the start of the process 706) to 100 percent (e.g., at the completion of the final iteration of process 708). In some additional embodiments, other types of visual representations, audible representations, or other representations may be configured to convey the progression towards completion of the collection of the plurality of measurement points 812.

At a process 714 and with reference to FIG. 14, when all regions or a predetermined sufficient number of regions have been surveyed, the collected plurality of measurement points 812 are registered to the model 600 of the anatomic structure of the patient P. The process for registration of the plurality of the measurement points 812 to the model space of the model 600 may include at least one of a global registration, a local registration, and/or a combination thereof. For instance, the collected plurality of measurement points 812 may be registered with the model space of the model 600 using a number of processes including the use of rigid and/or non-rigid transforms, a point set registration method (e.g., iterative closes point (ICP) technique), or any other number of registration processes within the scope of this disclosure. As shown in FIG. 14, the guidance information 802 may be updated to show the model 600 registered with an image of the elongate device 310.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Medical tools that may be delivered through the flexible elongate devices or catheters disclosed herein may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between its proximal and distal ends to controllably bend the distal end of the instrument. Steerable instruments are described in detail in U.S. Pat. No. 7,316, 681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The systems described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

In some instances, well known methods, procedures, components, and circuits have not been described in detail so as not to unnecessarily obscure aspects of the embodiments. This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
a medical instrument;
a tracking subsystem configured to receive position data from the medical instrument; and
a control system communicatively coupled to the medical instrument and the tracking subsystem, the control system configured to perform operations including:
accessing a model of an anatomic structure of a patient;
based on a determination that a real-time image of a known anatomical landmark within the anatomic structure of the patient matches a virtual image of the known anatomical landmark, receiving an indication that the medical instrument has been delivered to the known anatomical landmark within the anatomic structure of the patient;
based on receiving the indication that the medical instrument has been delivered to the known anatomical landmark, collecting a plurality of measurement points for a first anatomic region of a plurality of anatomic regions of the anatomic structure of the patient along a measurement path extending from a measurement initiation position proximate the known anatomical landmark within the anatomic structure of the patient as the medical instrument moves along the measurement path;
displaying, via a user interface, a progress indicator identifying a measurement collection progress of collecting the plurality of measurement points for the first anatomic region of the plurality of anatomic regions;
determining a location of the medical instrument relative to the anatomic structure of the patient;
based on the determined location of the medical instrument, determining a point collection threshold for the first anatomic region has been reached;
based on the point collection threshold for the first anatomic region being reached, providing operator instructions to collect a plurality of measurement points for a second anatomic region of the plurality of anatomic regions; and
registering the collected plurality of measurement points for the first anatomic region and collected plurality of measurement points for the second anatomic region to the model of the anatomic structure of the patient.

2. The system of claim 1 wherein the control system is further configured to perform an operation including:
providing a notification of a completion of the collection of the plurality of measurement points for the first anatomic region based at least on the determined location of the medical instrument.

3. The system of claim 1, wherein the control system is further configured to generate a virtual view of at least the known anatomical landmark based at least on the model of the anatomic structure of the patient, and wherein the user interface is configured to display the virtual view.

4. The system of claim 3, wherein the virtual view includes a first reference frame, wherein the medical instrument includes an imaging probe including a second reference frame, and wherein the user interface is configured to receive an input aligning the first reference frame and the second reference frame.

5. The system of claim 1, wherein the control system is configured to determine the point collection threshold for the first anatomic region has been reached further based at least on a quantity of the collected plurality of measurement points for the first anatomic region.

6. The system of claim 1, wherein the medical instrument includes an elongate device including an elongated flexible body, and wherein the plurality of measurement points are collected along a length of the elongate device while the elongate device is positioned within anatomy of the patient.

7. The system of claim 6, wherein the elongate device includes a shape sensor, and wherein the plurality of measurement points are collected from the anatomic structure of the patient using the shape sensor.

8. The system of claim 1, wherein the medical instrument includes an imaging probe.

9. The system of claim 8, wherein the indication that the medical instrument has been delivered to the known anatomical landmark is generated in response to vision recognition of the known anatomical landmark based on image data received from the imaging probe.

10. The system of claim 9, wherein the indication that the medical instrument has been delivered to the known anatomical landmark is generated automatically by the control system.

11. The system of claim 1, wherein the indication that the medical instrument has been delivered to the known anatomical landmark is received from a user input.

12. The system of claim 1, wherein the indication that the medical instrument has been delivered to the known anatomical landmark is received from the medical instrument.

13. The system of claim 12, wherein the indication that the medical instrument has been delivered to the known anatomical landmark is based upon an insertion depth.

14. The system of claim 13, wherein the insertion depth is determined by the tracking subsystem.

15. A non-transitory machine-readable medium comprising a plurality of machine-readable instructions which, when executed by one or more processors, are adapted to cause the one or more processors to perform a method comprising:
accessing a model of an anatomic structure of a patient;
based on a determination that a real-time image of a known anatomical landmark within the anatomic structure of the patient matches a virtual image of the known anatomical landmark, receiving an indication that a medical instrument has been delivered to the known anatomical landmark within the anatomic structure of the patient;
based on receiving the indication that the medical instrument has been delivered to the known anatomical landmark, collecting a plurality of measurement points for a first anatomic region of a plurality of anatomic regions of the anatomic structure of the patient along a measurement path extending from a measurement initiation position proximate the known anatomical landmark within the anatomic structure of the patient as the medical instrument is moves along the measurement path;
displaying, via a user interface, a progress indicator identifying a measurement collection progress of collecting the plurality of measurement points for the first anatomic region of the plurality of anatomic regions;
determining a location of the medical instrument relative to the anatomic structure of the patient;

based on the determined location of the medical instrument, determining a point collection threshold for the first anatomic region has been reached;

based on the point collection threshold for the first anatomic region being reached, providing operator instructions to collect a plurality of measurement points for a second anatomic region of the plurality of anatomic regions; and registering the collected plurality of measurement points for the first anatomic region and collected plurality of measurement points for the second anatomic region to the model of the anatomic structure of the patient.

16. The non-transitory machine-readable medium of claim 15, wherein the method further comprises providing a notification of a completion of the collection of the plurality of measurement points for the first anatomic region based at least on the determined location of the medical instrument.

17. The non-transitory machine-readable medium of claim 15, wherein the method further comprises generating a virtual view of at least the known anatomical landmark based at least on the model of the anatomic structure of the patient, and wherein the user interface is configured to display the virtual view.

18. The non-transitory machine-readable medium of claim 17, wherein generating the virtual view includes generating a first reference frame, wherein the medical instrument includes an imaging probe including a second reference frame, and wherein the user interface is configured to receive an input aligning the first reference frame and the second reference frame.

19. The system of claim 1, wherein the control system is further configured to perform an operation including:

displaying, via the progress indicator, that the point collection threshold for the first anatomic region has been reached.

20. The system of claim 1, wherein the progress indicator visually indicates a percent completion of the collecting the plurality of measurement points.

\* \* \* \* \*